United States Patent
Manker et al.

[11] Patent Number: 5,677,338
[45] Date of Patent: Oct. 14, 1997

[54] METHODS OF USING EMU OIL AND ACTIVE FRACTIONS THEREOF AS AN INSECT REPELLENT

[75] Inventors: Denise C. Manker; Pamela Gail Marrone; Stephen Judd, all of Davis, Calif.

[73] Assignee: AgraQuest, Inc., Davis, Calif.

[21] Appl. No.: 746,894

[22] Filed: Nov. 18, 1996

Related U.S. Application Data

[63] Continuation-in-part of Ser. No. 616,708, Mar. 15, 1996, Pat. No. 5,626,882.

[51] Int. Cl.[6] .................... A01N 37/02; A01N 37/06; A01N 63/00; A61K 35/12
[52] U.S. Cl. .................... 514/547; 514/546; 514/549; 514/558; 514/560; 514/919; 424/522; 424/DIG. 10
[58] Field of Search ................... 514/546, 547, 514/549, 558, 560, 919; 424/522, DIG. 10

[56] References Cited

U.S. PATENT DOCUMENTS

| | | | |
|---|---|---|---|
| 4,293,422 | 10/1981 | Still | 210/656 |
| 5,208,209 | 5/1993 | Otsuji et al. | 503/221 |
| 5,346,922 | 9/1994 | Bedlock et al. | 514/703 |
| 5,431,924 | 7/1995 | Ghosh et al. | 514/825 |
| 5,472,713 | 12/1995 | Fein et al. | 514/899 |

OTHER PUBLICATIONS

Wantanabe et al., "Rotundial, a new natural mosquito repellant from the leaves of *Vitex rotundifolia*" *Biotech Biochem.* (1995) 59(10):1979–1980.

Wantanabe et al., "New mosquito repellant from *Eucalyptus camaldulensis*" *J. Agric. Food Chem.* (1993) 41:2164–2166.

Sharma et al., "Mosquito repellant action of Neem (*Azadirachta indica*) oil" *J. Am. Mosquito Control Assn.* (1993) 9(3):359–360.

Still et al., "Rapid chromatographic technique for preparative separations with moderate resolution" *J. Organic Chem.* (1978) 43: 2923–2925.

PROMT Database, Accession No. 96: 342230 (1996).

Primary Examiner—John Pak
Attorney, Agent, or Firm—Morrison & Foerster LLP

[57] ABSTRACT

This invention provides a method for repelling biting insects such as mosquitoes by topically applying to the skin of a subject fractions of emu oil obtained by flash chromatography. Also provided are methods for repelling biting insects by topically applying diluted fractions of emu oil. The invention also provides a compound useful in repelling biting insects having the NMR spectrum of FIG. 3, that is ultra violet light sensitive and is reactive to vanillin/sulfuric acid. Also provided are compounds useful in repelling biting insects having the NMR spectrum of FIG. 4, that is not ultra violet light sensitive and is not reactive to vanillin/sulfuric acid.

2 Claims, 4 Drawing Sheets

METHODS OF USING EMU OIL AND ACTIVE FRACTIONS THEREOF AS AN INSECT REPELLENT

This application is a continuation-in-part application of U.S. patent application Ser. No. 08/616,708, filed on Mar. 15, 1996, now U.S. Pat. No. 5,626,882.

TECHNICAL FIELD

This invention is in the field of topical insect repellents. More particularly, effective, natural and safe mosquito repellents comprising fractionated emu oil are provided.

BACKGROUND ART

This invention relates to a method of repelling insects, and more particularly to a method for repelling mosquitoes using a natural ingredient, emu oil and active fractions thereof.

Known natural oils that repel insects include rotundial (from the leaves of *Vitex rotundifolia*, Watanabe K et al. (1995) *Biotech Biochem* 59(10):1979–1980); citronella oil (e.g. U.S. Pat. No. 5,346,922); eucalyptus oil (Watanabe et al. (1993) *J. Agric. Food Chem.* 41:2164–2166); neem oil (Sharma VP et al. (1993) *J. American Mosquito Control Association* 9(3):359–360); and oil of *Hedeoma pulgioides*, oil of anisum and oil of chrysanthemum (U.S. Pat. No. 5,208,209).

However, the compound most widely used as a topically-applied insect repellent is N,N-diethyl-m-toluamide (DEET). When applied to children's skin, DEET has been implicated in causing convulsions. DEET is also known to react with certain plastics and synthetic rubber and cause skin irritation (Watanabe et al. (1993), supra). As a result of these problems and other side effects, New York State had banned products comprised of 100% DEET.

The active fractions of the naturally occurring insect repellents are also largely unknown. Methods of resolving heterogeneous compounds into chemical species are well-known in the art. For example, silica gel flash chromatography provides for high speed resolution of organic compounds (see, e.g., U.S. Pat. No. 4,293,422). After separation, the eluted fractions can be recovered and tested for the activity of interest.

Accordingly, there remains a need for a natural, safe substance which acts to repel biting insects when topically applied to the skin. The active fraction(s) of such a substance is also needed.

SUMMARY OF THE INVENTION

The present invention provides a method for repelling biting insects comprising the step of topically applying emu oil or active fractions of emu oil to the skin of a subject.

BEST MODE FOR CARRYING OUT THE INVENTION

Figure 1:
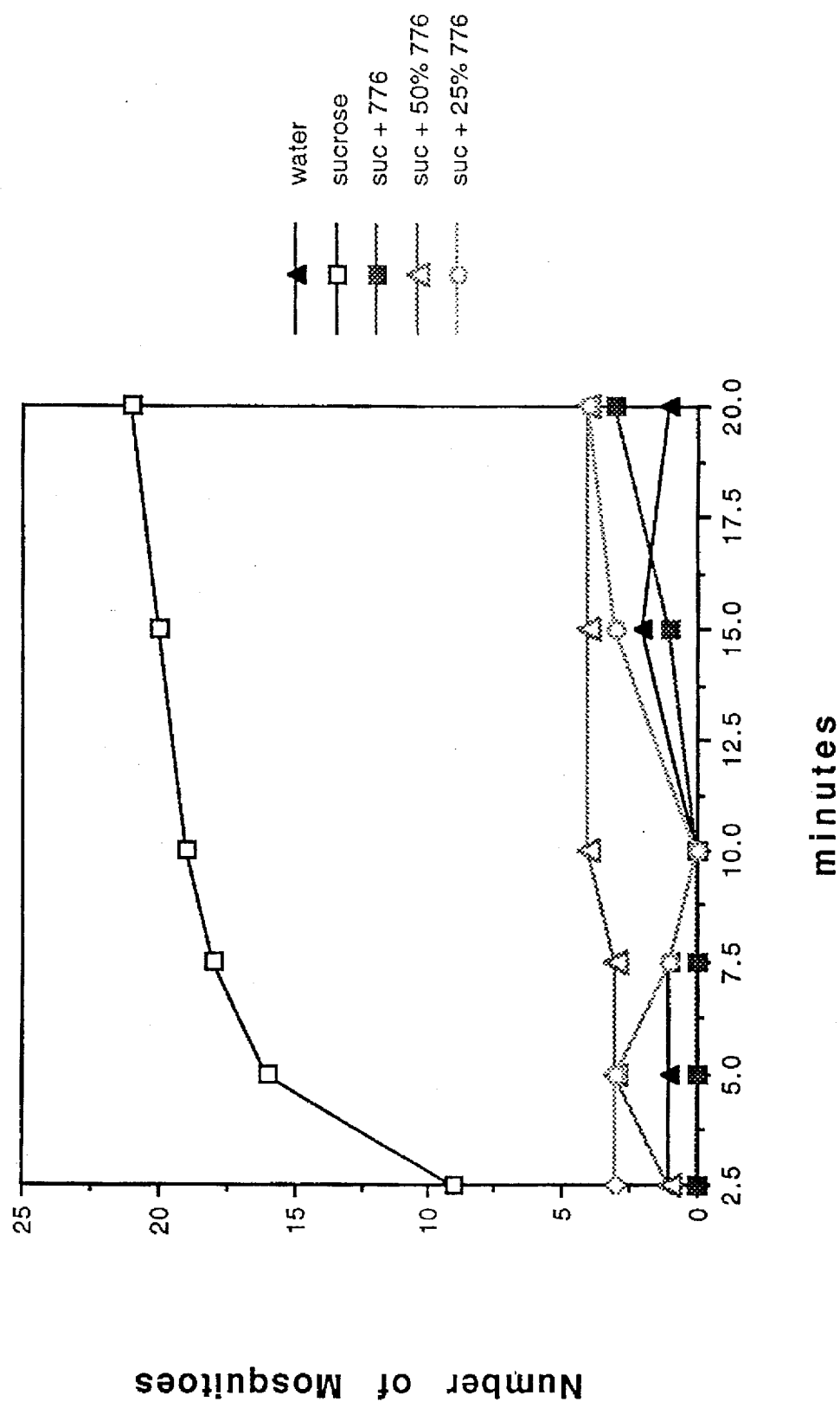
FIG. 1 shows the number of mosquitoes present on filter paper treated with water, sucrose or sucrose and diluted emu oil (sample 776) at 2.5 minute intervals. The solid triangles show water-treated filter paper controls. The open squares show sucrose-treated filter paper. The solid squares show sucrose-treated paper overlaid with undiluted sample 776. The open triangles show sucrose-treated paper overlaid with a 50% dilution of sample 776. The open circles show sucrose-treated paper overlaid with sample 776 diluted to 25%.

Throughout this application, various publications, patents and published patent applications are referred to by an identifying citation. The disclosures of these publications, patents and published patent applications are hereby incorporated by reference into this application to more fully describe the state of the art to which this invention pertains.

The present invention provides a method of repelling biting insects using emu oil, a natural and safe substance. In a preferred embodiment, pure emu oil is applied to the skin. In another preferred embodiment, diluted emu oil is topically applied. In yet another preferred embodiment, an active fraction of emu oil is applied to the skin.

The following examples are presented as a further guide to the practitioner of ordinary skill in the art, and are not to be construed as limiting the invention in any way.

EXAMPLES

Example 1

The effect of emu oil on frequency of mosquito lands and bites

To determine if emu oil was an effective mosquito repellent, pure emu oil (Zoogert, Inc., Davis, Calif.) was applied to one hand of a volunteer. The other hand was left untreated. Each hand was placed in a nylon mesh cage containing mosquitoes (*Aedes aegypti*) and the number of mosquitoes which landed and/or bit in 30 seconds was recorded. The experiment was performed in duplicate. Results of the experiments were averaged and are summarized in Table 1.

TABLE 1

|  | emu-oil treated hand (lands/bites) | untreated hand (lands/bites) |
| --- | --- | --- |
| Test 1 | 0/0 | 11/11 |
| Test 2 | 1/0 | 26/26 |

These results demonstrate that topically applied emu oil is an effective mosquito repellent. It greatly reduces the number of mosquitoes which land, and completely eliminates biting.

Example 2

The effectiveness of emu oil as a mosquito repellent over time

To determine how long topically applied emu oil maintains efficacy as a mosquito repellent, the treated hand was exposed to a cage of mosquitoes at 15, 30 and 60 minutes after application. The number of lands and bites were compared at each time point with the untreated hand. Results from duplicate experiments were averaged and are presented in Table 2.

TABLE 2

| Time after application | Number of lands on emu-oil treated hand | Number of lands on untreated hand |
|---|---|---|
| 15 | 4 | 18 |
| 30 | 2 | 12 |
| 60 | 10 | 12 |

These results show that emu oil remains an effective mosquito repellent for at least 30 minutes.

Example 3

The effectiveness of diluted emu oil

To determine the effectiveness of diluted emu oil, the emu oil was diluted with ethyl acetate to a fixed percentage, applied to one hand and inserted into a mosquito cage. The number of lands were recorded. The experiments were performed in duplicate at each dilution level. Results are shown in Table 3.

TABLE 3

| Percent emu oil | Number of lands Exp't 1 | Number of lands Exp't 2 | Average Number of lands |
|---|---|---|---|
| 0 | 10 | 9 | 9.5 |
| 0.50 | 10 | 10 | 10 |
| 1.0 | 5 | 5 | 5 |
| 5.0 | 6 | 4 | 5 |
| 10.0 | 4 | 5 | 4.5 |
| 25.0 | 2 | 1 | 1.5 |
| 50.0 | 1 | 1 | 1 |
| 75.0 | 1 | 1 | 1 |
| 100.0 | 0 | 0 | 0 |

These results demonstrate that dilute amounts of emu oil effectively repel mosquitoes. At a dilution as low as 1%, emu oil reduces by one-half the number of mosquitoes which land. At 25% emu oil, the number of mosquito lands drops to one-tenth of lands on an untreated hand. Thus, emu oil is an effective insect repellent at a concentration of 1% or higher.

Example 4

Fractionation of emu oil and the effectiveness of the fractions

Figure 3:
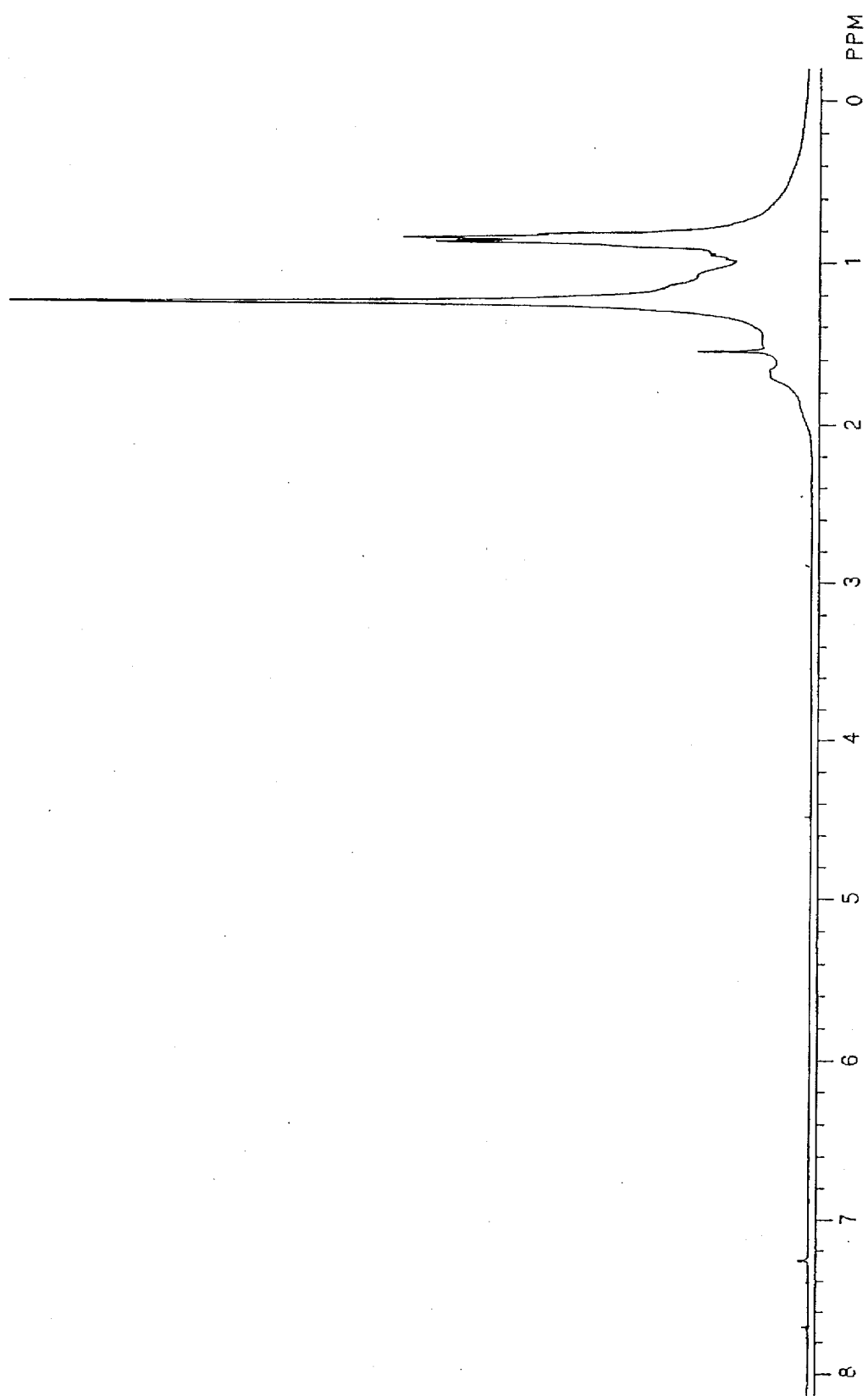
FIG. 3 shows the $^1$H NMR spectrum of the F1 fraction of emu oil.
Figure 4:
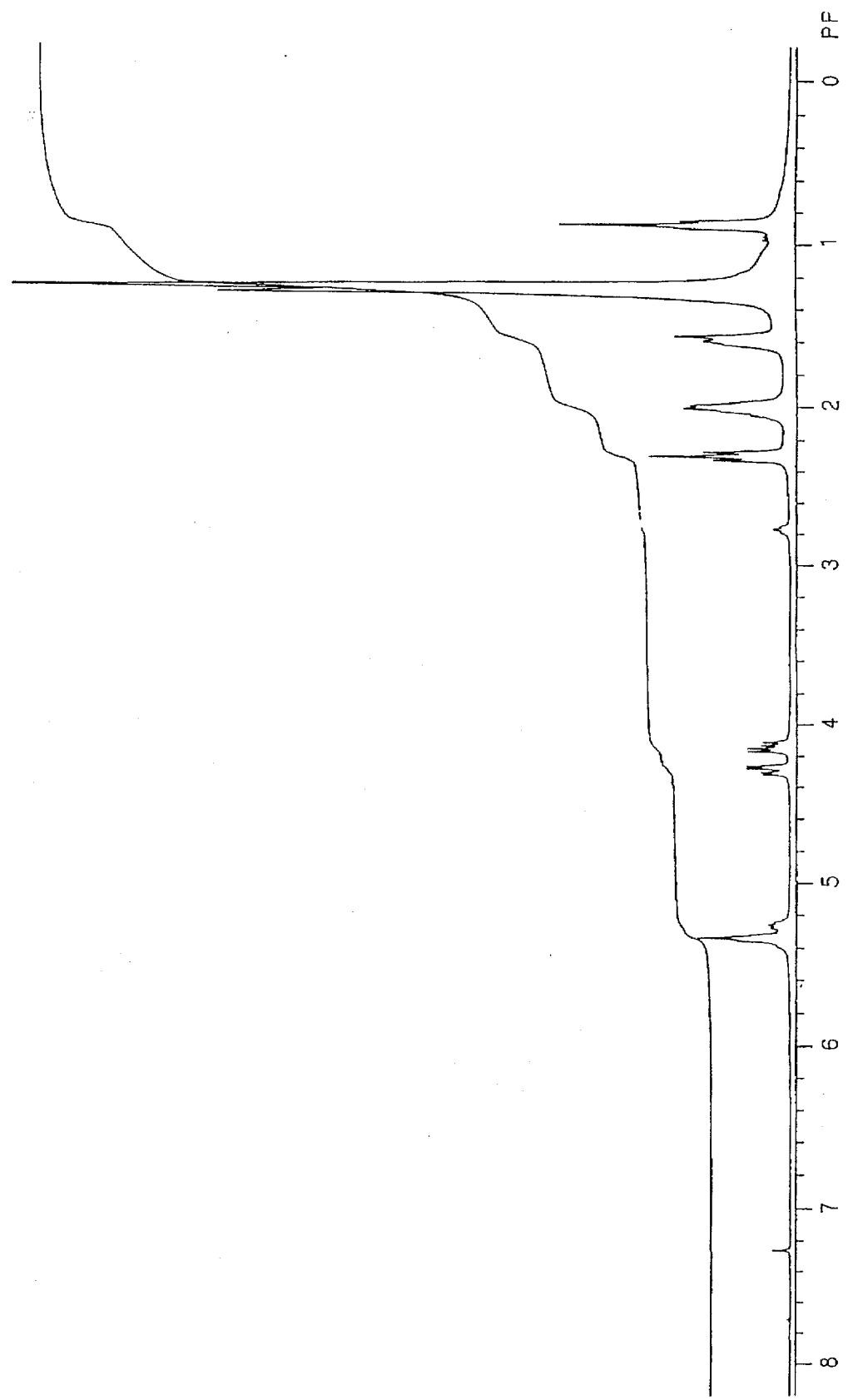
FIG. 4 shows the $^1$H NMR spectrum of the F2 fraction of emu oil.

An 850 mg sample (776) of emu oil was steam-distilled and fractionated using silica flash chromatography (Baker silica gel, 40 µm), essentially as described in Still et al. (1978) *J. Organic Chem.* 43:2923. Two major components of the sample were eluted from the column with 100% hexane and 25% ethyl acetate/hexane. Fractions were analyzed by thin layer chromatography (TLC) on silica plates developed with 50% hexane/ethyl acetate. Components on the TLC plates were observed by exposing the plates to UV light (indicating UV chromophores) and spraying plates with vanillin/sulfuric acid (indicating the presence of higher alcohols, sterols, phenols or essential oils). 430 mg of a clear oil, termed F2, was found to be UV active and reactive to vanillin/sulfuric acid. The second component, 380 mg of a pale yellow oil termed F1, was not UV active and did not stain with vanillin. F1 and F2 fractions were analyzed by $^1$H NMR (300 MHz, CDCl$_3$) as shown in FIGS. 3 and 4.

A mosquito repellent bioassay was performed by treating wedges of filter paper with sucrose overlaid with either an aliquot of the crude sample 776, F1 or F2. Filter paper treated with water or sucrose served as controls. Samples of F1 and F2 were tested at full-strength or diluted with corn oil to 50% or 25% of full-strength. At regular time intervals, the number of mosquitoes which landed and fed on the wedges of filter paper was recorded. Results are shown in FIGS. 1 and 2.

Figure 2:
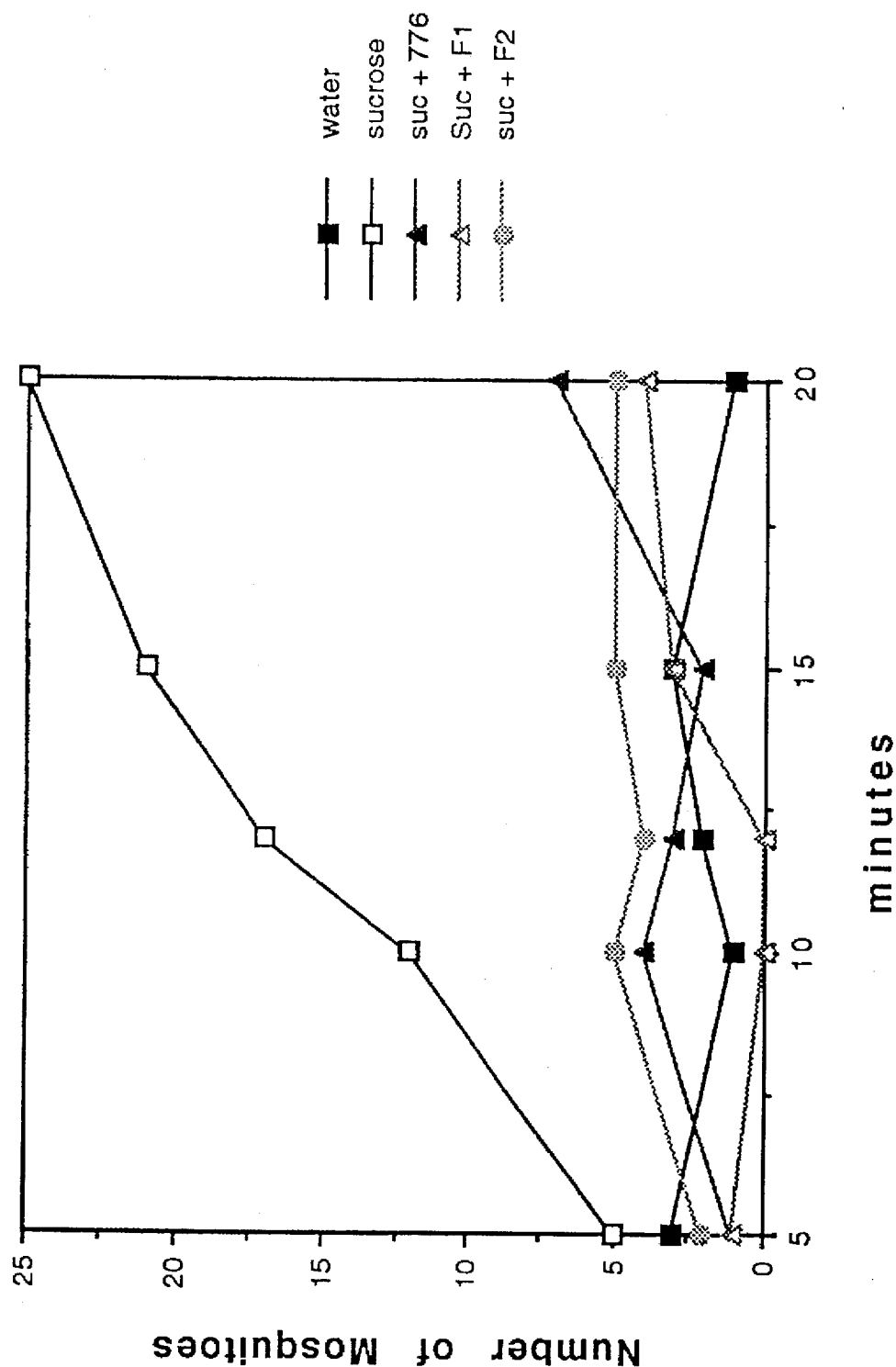
FIG. 2 shows the number of mosquitoes present on filter paper treated with water, sucrose, or sucrose and fractions of sample 776 at 5 minute intervals. The solid squares show water-treated paper. The open squares show sucrose-treated paper overlaid. The solid triangles show sucrose-treated paper overlaid with a sample 776. The open triangles show sucrose-treated paper overlaid with fraction F1. The solid circles show sucrose-treated paper overlaid with fraction F2.

As shown in FIG. 1, even diluted to 25% of full-strength, the crude sample (776) greatly reduces the number of mosquitoes landing on the sucrose paper. In addition, FIG. 2 shows that both the F1 and F2 fractions of sample 776 at full-strength and diluted to 50% or 25% of full-strength were effective in repelling mosquitoes when compared to the sucrose-treated control.

Example 5

The effect of emu oil as a tick repellent

To determine if emu oil was an effective tick repellent, a test subject's hands were treated with emu oil while the fingers of the hand were left untreated. As a positive control, Ultrathon (3M, Minneapolis, Minn.) was applied to the hand and the fingers were left untreated. An untreated hand was used as a negative control. Unfed nymphal Western Black-legged ticks were placed on the fingers of the hands and observed as they climbed toward the treated or untreated skin of the hand. Ticks crossing onto the treated skin were scored as "crossing." Those not crossing were scored as "repelled." Ticks were removed after a single score was recorded. Repellency is calculated as the proportion of all trials in which a tick is repelled. For example, 8 repels in 10 trials provides a repellency of 80%. In this study, each subject tested a tick at 15 flute intervals for 2 hours and 15 minutes. The results are shown below:

Negative control—untreated skin—0% repellency

Positive control Ultrathon (3M)—70% repellency

Emu oil—40% repellency

There was no indication that the repellency declined over the two hour test period.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows the scope of the appended claim.

What is claimed is:

1. A method for repelling biting insects comprising the step of topically applying to the skin of a subject in need of repellence of biting insects a fraction of emu oil obtained by flash chromatography having the $^1$H NMR (300 MHz, CDCl$_3$) spectrum of FIG. 3 and that is ultra violet light active and reactive to vanillin/sulfuric acid.

2. The method of claim 1 wherein the emu oil fraction is diluted.

* * * * *

UNITED STATES PATENT AND TRADEMARK OFFICE
CERTIFICATE OF CORRECTION

PATENT NO. : 5,677,338

DATED : October 14, 1997

INVENTOR(S) : Manker et al.

It is certified that error appears in the above-identified patent and that said Letters Patent is hereby corrected as shown below:

At column 3, line 60, delete "F2" and replace with --F1--.

At column 3, line 62, delete "F1" and replace with --F2--.

Signed and Sealed this

Twenty-fourth Day of November, 1998

Attest:

BRUCE LEHMAN

Attesting Officer

Commissioner of Patents and Trademarks